(12) United States Patent
Brade et al.

(10) Patent No.: US 9,678,094 B2
(45) Date of Patent: Jun. 13, 2017

(54) APPARATUS AND METHOD FOR DETERMINING THE POSITION OF AN AUTOMATICALLY DISPLACEABLE GAUGE

(71) Applicant: Siemens Healthcare Diagnostics Products GmbH, Marburg (DE)

(72) Inventors: Carolin Brade, Eppertshausen (DE); Dirk Bugner, Mainz (DE); Guenther Kotulla, Frankfurt (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 14/802,867

(22) Filed: Jul. 17, 2015

(65) Prior Publication Data
US 2016/0018430 A1   Jan. 21, 2016

(30) Foreign Application Priority Data
Jul. 21, 2014   (EP) .................................... 14177778

(51) Int. Cl.
*G01N 35/10* (2006.01)
*G01N 35/02* (2006.01)

(52) U.S. Cl.
CPC ..... *G01N 35/1011* (2013.01); *G01N 35/1009* (2013.01)

(58) Field of Classification Search
CPC . Y10T 436/11; Y10T 436/00; G01N 35/1011; G01N 35/1009; G01N 35/10; G01N 35/025; G01N 35/02; G01N 35/00

USPC .................................. 436/43; 422/63, 37, 50
See application file for complete search history.

(56) References Cited

U.S. PATENT DOCUMENTS

| 4,276,258 | A | 6/1981 | Ginsbert et al. |
| 5,317,351 | A | 5/1994 | Takahara |
| 5,529,754 | A | 6/1996 | Bonacina et al. |
| 2014/0016841 | A1 | 1/2014 | Zahniser et al. |

FOREIGN PATENT DOCUMENTS

DE   10-2008-058065   5/2010

OTHER PUBLICATIONS

European Search Report of European Application No. 14177778.9 dated Sep. 26, 2014.

*Primary Examiner* — Christine T Mui
(74) *Attorney, Agent, or Firm* — Dugan & Dugan, PC

(57) ABSTRACT

The invention relates to apparatus for determining the position of an automatically displaceable gauge. The apparatus comprises the gauge, a first device for displacing the gauge in the spatial X-direction, a second device for displacing the gauge in a spatial Z-direction, a sensor for identifying the abutment of the gauge on, or the approach thereof to, an article, an at least partly bordered receptacle position, into which the gauge is at least partly insertable by displacing the gauge in the spatial X- and/or Z-direction, and a movable assembly, wherein the receptacle position for the gauge is arranged on the movable assembly.

18 Claims, 7 Drawing Sheets

APPARATUS AND METHOD FOR DETERMINING THE POSITION OF AN AUTOMATICALLY DISPLACEABLE GAUGE

CROSS REFERENCE TO RELATED APPLICATION

This claims priority to European Patent Application No. EP 14177778.9, filed Jul. 21, 2014, which is hereby incorporated by reference herein in its entirety for all purposes.

FIELD

The invention relates to apparatus, suitable for an analysis instrument, for determining the position of a gauge and a method for determining the position.

BACKGROUND

These days, numerous detection and analysis methods for determining physiological parameters in bodily fluid samples or other biological samples are performed in a large number and in an automated manner in automatic analysis instruments, also so-called in vitro diagnostic systems.

Current analysis instruments are able to perform a multiplicity of detection reactions and analyses using one sample. In order to be able to perform a multiplicity of examinations in an automated manner, various devices for the spatial transfer of measurement cells, reaction containers, and reagent containers are necessary, such as, e.g., transfer arms with a gripper function, transport belts, or rotatable transport wheels, as are devices for transferring liquids, such as, e.g., pipetting devices. The instruments comprise a control unit which, by means of appropriate software, is able to plan and work through the work steps for the desired analyses in a largely independent manner.

Many of the analysis methods used in such analysis instruments operating in an automated manner are based on optical processes. These methods render possible the qualitative and quantitative detection of analytes, i.e., the substances in samples to be detected or determined. Clinically relevant parameters, such as, e.g., the concentration or activity of an analyte, are often determined by virtue of part of the sample being mixed with one or more test reagents in a reaction vessel, which can also be the measurement cell, as a result of which, for example, a biochemical reaction or a specific binding reaction is initiated, which brings about a measurable change of an optical or other physical property of the test run.

Samples can be fed to analysis instruments in sample collection tubes, which are sealed by a seal that can be pierced by a needle. Alternatively, the sample collection tubes can also be open or opened prior to being fed to the analysis instrument. In the analysis instrument, parts of the sample or the whole sample can be taken from the sample collection tube by means of a needle and transferred into other containers. Here, an exact alignment of the needle is necessary as the needle must hit the often relatively small opening or the relatively small seal of the sample collection tube and, at the same time, should not touch the edge of the sample collection tube in order, for example, to avoid the needle bending. Furthermore, it is necessary for the pipetting needle to hit relatively small openings of cuvettes, washing stations, or retaining devices precisely. Sample tubes and reaction vessels can be situated in receptacle positions on a linearly movable or rotatable assembly.

In particular, modern analysis instruments can be equipped with apparatus for determining the position for pipetting needles. Using this, it is possible to adjust pipetting needles and, in part, also monitor these for bending, as may occur through use or collisions. Furthermore, the correct assembly after replacing a pipetting needle can be verified, for example, by determining the position of the pipetting needle tip. If need be, a deviation in the position of the pipetting needle tip from the intended position can also be achieved by an appropriate displacement of the pipetting needle. A pipetting needle is usually assembled on a transfer arm.

Interacting assemblies, such as, e.g., a linearly movable assembly or a rotatable assembly with receptacle positions for sample tubes and, e.g., a linearly movable transfer arm with a pipetting needle, a gripper, or a gauge must be precisely adjusted relative to one another. Here, the linearly movable assembly and the linearly movable transfer arm or the rotatable assembly and the linearly movable transfer arm can be arranged at different angles to one another. By way of example, in an automatic analysis system, a rotatable assembly can also interact with a plurality of linearly movable transfer arms, which are located at different angles in relation to the rotatable assembly. For adjustment purposes, use is usually made of a plurality of reference abutment points with known position coordinates. The interacting assemblies are usually adjusted by hand by a skilled service technician, which often means significant outlay and is connected with high costs.

SUMMARY

It is therefore an object of the invention to provide apparatus for determining the position for a precise automatic adjustment of interacting assemblies in an analysis instrument, wherein the adjustment can be implemented independently of the angles at which the interacting assemblies are arranged with respect to one another.

According to the invention, the object is achieved by the methods and subject matter described below.

It was found that a precise automatic adjustment of interacting assemblies is possible by means of specifically shaped receptacle positions, which consist, e.g., of metal or a conductive plastic and which are arranged on movable assemblies and which, for example, can be detected by means of capacitive processes using a conducting gauge.

Subject matter of the present invention relates to apparatus for determining the position of an automatically displaceable gauge, said apparatus comprising at least one gauge, a first device for displacing the gauge in the spatial X-direction, which is perpendicular to the longitudinal axis of the gauge, and a second device for displacing the gauge in a spatial Z-direction, which extends parallel to the longitudinal axis of the gauge, and a sensor for identifying the abutment of the gauge on, or the approach thereof to, an article, and an at least partly bordered receptacle position for the gauge, into which the gauge is at least partly insertable by displacing the gauge in the spatial X- and/or Z-direction, and a movable assembly. The receptacle position for the gauge is arranged on the movable assembly.

An advantage of this is that the previously necessary, complicated manual determination of the position, in particular after replacing gauges, can be dispensed with. This also results in significant cost advantages.

Furthermore, a deviation from the perpendicular position of the gauge can be established by virtue of the position of the gauge being established in the spatial X- and/or Y-direction at various positions along the gauge. Here, the gauge should also be displaced appropriately in the spatial Z- and/or −Z-direction.

The at least one movable assembly can be linearly or rotatably movable. Advantageously, the assembly can be moved in the positive and/or negative direction.

BRIEF DESCRIPTION OF THE DRAWINGS

The embodiments depicted in the figures in an exemplary manner are intended to elucidate the present invention and should not be construed as being restrictive. In detail.

Figure 1:
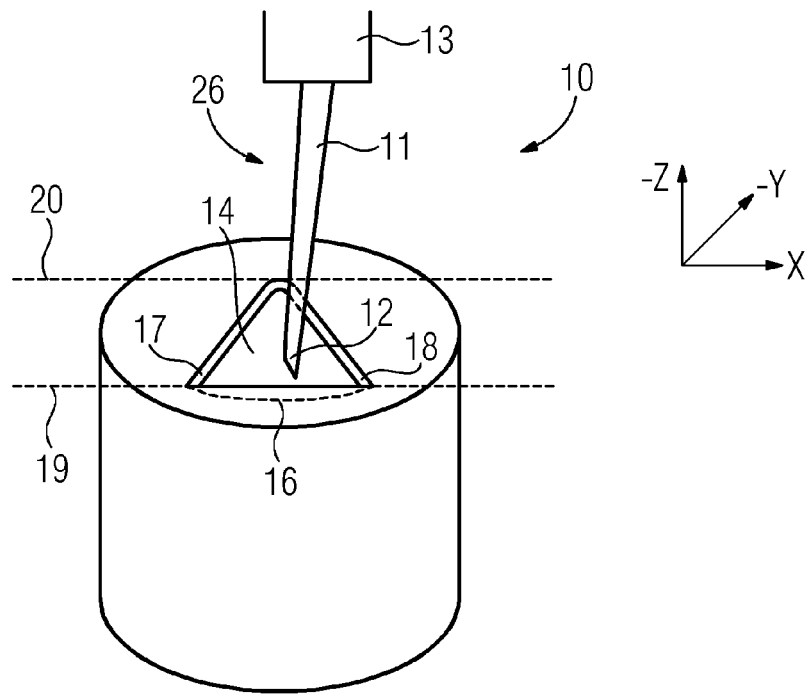
FIG. 1 shows apparatus for determining the position for a gauge.

Equivalent parts of being provided with the same reference sign in all figures.

DETAILED DESCRIPTION

In a preferred embodiment, at least one movable assembly has a rotatable configuration and can be rotated in at least an angular range within 0 and 360 degrees in respect of the polar angle (azimuth). In a further advantageous configuration, the movable assembly has a rotatable configuration and can be rotated through at least 360 degrees in respect of the polar angle (azimuth). In a particularly preferred embodiment, the rotatable assembly is revolvable. Advantageously, the rotation can be implemented in the positive and/or negative direction.

In a preferred embodiment of the apparatus according to the invention for determining the position, the receptacle position for the gauge has a first edge section and a second edge section, wherein the edge sections delimit the receptacle position for the gauge in the spatial X-direction in such a way that the receptacle position for the gauge decreases strictly monotonically between a first imaginary line, which extends parallel to the spatial X-direction, and a second imaginary line, which extends parallel to the spatial X-direction, in the spatial X-direction, which extends tangentially to the rotatable assembly in the region of the device for determining the position. This is advantageous in that the position can be determined more quickly by means of comparatively few method steps and in that the previously necessary displacement of the gauge in two spatial directions X and Y for determining the position in the two spatial directions X and Y, in particular after replacing the gauge, can be dispensed with.

In a further preferred embodiment of the apparatus according to the invention for determining the position, the receptacle position for the gauge has the shape of a triangle, preferably the shape of an isosceles triangle, or the shape of a digon, similar or equal in shape to an isosceles triangle with a rounded section between the sides, or the shape of a half circular disk or the shape of a quarter circular disk.

Triangular shapes of the receptacle position are advantageous since these can be manufactured in a particularly simple and cost-effective manner, e.g., by means of injection molding technology.

Receptacle positions with rounded or round sections can be manufactured particularly easily by means of milling methods.

Isosceles embodiments of the triangle or configurations of the receptacle position as, e.g., a half or quarter circular disk are advantageous since a comparatively large area is comprised by the receptacle position and therefore gauges which were only pre-adjusted in a comparatively imprecise manner can also be displaced automatically into the receptacle position and can be adjusted automatically.

Advantageously, the angles of the isosceles triangle are selected as a function of the diameter of the gauge in such a way that the travel of the gauge in the spatial X-direction between the sides of the triangle up to the respective abutment of the gauge at the sides is a function of the position of the gauge in the spatial Y-direction such that, when there is a change in the position of the gauge in the spatial Y-direction by the first value, e.g., 1 mm, there is a change in the travel of the gauge in the spatial X-direction between the sides of the triangle by likewise the first value. It is possible, depending on the selection of the orientation of the coordinate system, for the change in the position of the gauge in the spatial Y-direction and the change in the travel of the gauge in the spatial X-direction between the sides of the triangle to have either the same sign or the respective other sign.

As a result of the very simple relationship between the change in the position of the gauge in the spatial Y-direction and the change of the travel of the gauge in the spatial X-direction between the sides of the triangle provided thus, there is no need for a complicated and time-consuming calculation in order, for example, to determine the position of the gauge in the spatial Y-direction in the case of a given travel of the gauge in the spatial X-direction.

In a further preferred embodiment of the apparatus according to the invention for determining the position, the receptacle position for the gauge has a first edge section and a second edge section, wherein the first edge section and the second edge section of the receptacle position for the gauge extend in a straight line and converge in a V-shape and wherein the first edge section and the second edge section are symmetrical with respect to the straight extended connection line between the point of rotation of the rotatable assembly and the point at which the first edge section and the second edge section converge. Here, the receptacle position is oriented on the rotatable assembly in such a way that the receptacle position opens outward in the radial direction. By way of example, this is advantageous in that a gauge can be displaced into the receptacle position without a movement in the spatial Z-direction, which is parallel to the axis of rotation of the rotatable assembly and/or the longitudinal axis of the gauge. The aperture angle between the first edge section and the second edge section is preferably between 20 and 140 degrees, particularly preferably between 60 and 100 degrees, very particularly preferably 80 degrees.

In a further preferred embodiment of the apparatus according to the invention for determining the position, the receptacle position for the gauge is configured as a depression in the form of a cylinder, preferably a right circular cylinder. This is advantageous in that the receptacle position can be manufactured in a particularly simple and cost-effective manner. In a further preferred embodiment, the depression has at least one further depression, which is preferably situated in the center and/or at the edge of the depression.

In a further preferred embodiment of the apparatus according to the invention for determining the position, the receptacle position for the gauge has at least one step, preferably at least two steps with respectively a boundary face in the spatial Z-direction, the normal of which extends parallel to the spatial Z-direction. This is advantageous in that the position of the gauge can also be determined in the spatial Z-direction. In addition to the position of the boundary face or the positions of the boundary faces in the spatial Z-direction, it is, for example, also possible to evaluate the height of the step or the steps in the adjustment method. This enables a particularly precise, robust determination of the position in the spatial Z-direction, with a comparatively small susceptibility to errors.

In a further preferred embodiment of the apparatus according to the invention for determining the position, the receptacle position for the gauge has at least one boundary face, the normal of which extends perpendicular to the spatial Z-direction and, for example, parallel to the spatial Y-direction, wherein the spatial Y-direction extends perpendicular to the movement direction of the movable assembly, or in the radial direction in the case of a rotatable assembly. In a preferred embodiment, the boundary face is situated between two of the boundary faces in the spatial Z-direction which form a step.

In a preferred embodiment, the gauge is embodied as a cylinder, preferably as a right circular cylinder, or the gauge is a gripper or the gauge is a pipetting needle. By way of example, apparatus for determining the position can also comprise two or more gauges. By way of example, the two or more gauges can comprise at least one gripper and/or one pipetting needle.

Another subject matter of the invention relates to an analysis instrument with movable assemblies, comprising apparatus according to the invention for determining the position of an automatically displaceable gauge.

An analysis instrument according to the invention advantageously comprises apparatus for the spatial transfer of measurement cells, reaction containers and reagent containers, such as, e.g., transfer arms with a gripper function, transport belts or rotatable transport wheels, or for the transfer of liquids, such as, e.g., pipetting devices with pipetting needles. Advantageously, an analysis instrument according to the invention furthermore comprises a control unit which, by means of appropriate software, is able to plan and work through the work steps for the desired analyses in a largely independent manner.

Further subject matter of the present invention relates to a method for determining the position of an automatically displaceable gauge, comprising the following method steps:
a) introducing the gauge into a receptacle position, which is arranged on a movable assembly, by displacing the gauge in the spatial Z-direction, which extends parallel to the longitudinal axis of the gauge, and/or in the spatial X-direction, which extends parallel to the movement direction of the movable assembly, and/or in the spatial Y-direction, which extends perpendicular to the movement direction of the movable assembly;
b) moving the movable assembly in the positive direction until the gauge approaches, or abuts on, a first edge section of the receptacle position;
c) moving the movable assembly in the negative direction until the gauge approaches, or abuts on, a second edge section of the receptacle position; and
d) establishing the distance between the first edge section and the second edge section of the receptacle position.

In a further preferred embodiment, a method according to the invention for determining the position of an automatically displaceable gauge additionally comprises the following steps:
e) establishing the position of the gauge in the spatial X-direction by evaluating the abutment point at the first edge section and/or the abutment point at the second edge section of the receptacle position;
f) establishing the position of the gauge in the spatial Y-direction by assigning the established distance between the abutment point on the first edge section and the abutment point on the second edge section of the receptacle position to a position in the spatial Y-direction.

A first position X1 of the gauge in the spatial X-direction is established by moving the movable assembly in the positive direction until the gauge approaches, or abuts on, the first edge section of the receptacle position. A second position X2 of the gauge in the spatial X-direction is established by moving the movable assembly in the spatial minus X (−X) direction until the gauge approaches, or abuts on, the second edge section of the receptacle position. The extent of the receptacle position in the spatial X-direction therefore emerges from the distance between X1 and X2. The precise position of the gauge in the spatial Y-direction can be deduced by means of the extent of the receptacle position in the spatial X-direction, established thus, as a result of the known shape and orientation of the receptacle position on the movable assembly. The exact position of the gauge in the spatial X-direction emerges by evaluating the position X1 and/or the position X2. After determination of the position is complete, the gauge can, for example, be removed from the receptacle position by displacing the gauge in the spatial X-, Y- and/or Z-directions.

When establishing and evaluating the distance between the X1 position and the X2 position, the extent of the cross section of the gauge in the spatial X- and Y-directions and, where applicable, the shape of the cross section of the gauge should advantageously also be noted. The extent of the gauge may possibly be neglected, for example, in the case of a very thin needle or if the acceptable tolerance when determining the position is large relative to the extent of the cross section of the gauge.

In a further preferred embodiment, a method according to the invention for determining the position of an automatically displaceable gauge additionally comprises the following steps:
g) displacing the gauge in the spatial Y-direction within the receptacle position;
h) repeating steps b), c), d);
i) establishing the position of the gauge in the spatial Y-direction by assigning the established distances between the abutment points on the first edge section and the abutment points on the second edge section of the receptacle position to a position in the spatial Y-direction.

This is advantageous in that the position can also be determined by means of a receptacle position for the gauge which, for example, has the shape of a right circular cylinder. In particular, the receptacle position for the gauge of this preferred embodiment of the method according to the invention for determining the position need not necessarily have a first edge section and a second edge section, wherein the edge sections delimit the receptacle position for the gauge in the spatial X-direction in such a way that the receptacle position for the gauge decreases strictly monotonically between a first imaginary line, which extends parallel to the spatial X-direction, and a second imaginary line, which extends parallel to the spatial X-direction, in the spatial X-direction, which extends tangentially to the rotatable assembly in the region of the device for determining the position.

In a further preferred embodiment, the method according to the invention additionally comprises the following steps:
j) displacing the gauge in the spatial Y-direction within the receptacle position until the gauge approaches, or abuts on, a boundary face of the receptacle position, the normal of which extends parallel to the spatial Y-direction, and
k) establishing the position of the gauge in the spatial Y-direction by evaluating the abutment point of the gauge at the boundary face of the receptacle position, the normal of which extends parallel to the spatial Y-direction.

This is advantageous in that a determination of the position or an approximate determination of the position of the gauge in the spatial Y-direction, which extends perpendicular to the movement direction of the movable assembly, or in the radial direction in the case of a rotatable assembly, can be implemented comparatively quickly, in an uncomplicated manner and, for example, also independently of other method steps. Consequently, it is possible to compare the positions of the gauge in the spatial Y-direction which were determined by different methods and independently from one another. By way of example, this also increases the reliability and robustness of a method according to the invention for determining the position.

In a further preferred embodiment of the method according to the invention, the movable assembly is rotatable, wherein the spatial X-direction extends tangentially to the rotatable assembly and wherein the spatial Y-direction extends radially to the rotatable assembly.

In a further preferred embodiment of the method according to the invention, the receptacle position for the gauge has the shape of a triangle, preferably the shape of an isosceles triangle, or the shape of a digon, similar or equal in shape to an isosceles triangle with a rounded section between the sides, or the shape of a half circular disk or the shape of a quarter circular disk.

In a further preferred embodiment of the method according to the invention, the first edge section and the second edge section of the receptacle position for the gauge extend in a straight line and converge in a V-shape, wherein the first edge section and the second edge section are symmetrical with respect to the straight extended connection line between the point of rotation of the rotatable assembly and the point at which the first edge section and the second edge section converge.

The target position of an adjustment by means of a method according to the invention for determining the position is distinguished, for example, by the bisector of the V-structure and by the expected edge length. By way of example, the target position is established by combined linear movement of the gauge and rotational movement of the rotatable assembly.

In a further preferred embodiment of the method according to the invention, the receptacle position for the gauge is configured as a depression in the form of a cylinder, preferably a right circular cylinder.

In a further preferred embodiment of the method according to the invention, the receptacle position for the gauge has at least one step, preferably at least two steps with respectively a boundary face in the spatial Z-direction.

In a further preferred embodiment of the method according to the invention, the receptacle position for the gauge has at least one boundary face situated between two of the boundary faces in the spatial Z-direction, the normal of which extends perpendicular to the spatial Z-direction and, for example, parallel to the spatial Y-direction, wherein the spatial Y-direction extends perpendicular to the movement direction of the movable assembly or in the radial direction in the case of a movable assembly that is rotatable (i.e., a rotatable assembly).

In a further preferred embodiment of the method according to the invention, the gauge is embodied as a cylinder, preferably as a right circular cylinder, or the gauge is a gripper or a pipetting needle.

The approach of the gauge to the edge of the receptacle position, or the abutment thereon, is detected by means of a suitable sensor.

In a preferred embodiment, the approach of the gauge to the edge of the receptacle position, or the abutment thereon, is established by means of capacitive measurement processes. This is possible, in particular, if the gauge and the edge of the receptacle position consist of an electrically conductive material. Advantageously, an already available functionality for capacitive level detection of liquids by means of a conductive pipetting needle can also be used in this respect.

Here, in an alternative embodiment, in each case only at least one edge section of the receptacle position and/or at least one part of the gauge consists of an electrically conductive material.

The method is applicable if the approximate position of the pipetting needle relative to the position of the movable assembly is known well enough in advance to the extent that the gauge can be displaced into the receptacle position. This condition can be satisfied by a suitable selection of the extent and/or the aperture angle of the receptacle position.

Advantageously, the subjects and methods according to the invention are used for adjusting a pipetting needle, preferably the tip of a pipetting needle, relative to a rotatable assembly with receptacle position for sample tubes. Advantageously, the receptacle positions for sample tubes are suitable for receiving respectively one sample tube with a round, oval, and/or polygonal cross section. Advantageously, the rotatable assembly comprises one or at least two receptacle positions for sample tubes.

In a preferred embodiment of the movable assembly, the at least two receptacle positions for sample tubes are arranged along a circular path, preferably in at least two concentric circular paths. By way of example, this is advantageous in that a larger number of receptacle positions can be arranged per unit area. Furthermore, this can increase the sample throughput.

A sample tube can be, e.g., a measurement cell or a cuvette, which often consists of glass, plastic or quartz glass. In one configuration of the movable assembly according to the invention, it is also possible for flow cuvettes to be used as sample tubes.

Within the meaning of the present invention, a pipetting needle should be understood to mean a needle, e.g., made of metal or electrically conductive plastic, for pipetting liquid samples and/or liquid reagents in an analysis instrument. In preferred configurations, the cross section of the pipetting needle is round or approximately round or oval or approximately oval.

The terms "needle" and "pipetting needle" are used synonymously.

Within the meaning of the invention, a "sample" is to be understood to mean the material which presumably contains a substance to be detected (the analyte). In particular, the term sample comprises biological liquids of humans or animals, such as, e.g., blood, plasma, serum, sputum, exudates, bronchoalveolar lavage, lymph fluid, synovial fluid, semen, vaginal mucus, feces, urine, liquor, or else e.g., tissue or cell culture samples prepared by homogenization or cell lysis. Furthermore, plant liquids or tissues, forensic samples, water and sewage samples, foodstuff, pharmaceuticals may also serve as a sample which, possibly, should be subject to an appropriate sample pretreatment prior to the determination.

In addition to the exact spatial direction, specifications in respect of the spatial X-, Y-, Z-directions also mean the spatial direction which deviates by up to 20 degrees, preferably by up to 10 degrees, very preferably by up to 5 degrees, in relation to the precise spatial direction.

The subjects and methods according to the invention of the present patent application are, moreover, described in the patent claims.

FIG. 1 illustrates, in an exemplary manner, apparatus (10) according to the invention for determining the position for a gauge (26), wherein the gauge (26) is a pipetting needle (11), with a pipetting needle tip (12), fastened to a suspension (13). The apparatus (10) for determining the position is embedded in an analysis instrument (not depicted in any more detail) which is configured to implement a multiplicity of analyses of samples. To this end, the automatic analysis instrument comprises a multiplicity of transport apparatuses (not shown here) and, furthermore, a control unit for automated evaluation of the analyses.

The apparatus (10) for determining the position for a gauge (26) comprises a recess which constitutes the receptacle position (14) for the pipetting needle (11). The receptacle position (14) has an edge (16) and a specifically configured shape. The edge (16) extends partly in parallel with the imaginary lines (19, 20) and has a first edge section (17) and a second edge section (18). Here, the pipetting needle (11) is at least displaceable in the spatial X- and Z-directions by means of the suspension (13) of the pipetting needle. The receptacle position (14) is arranged on a movable assembly (27) (not shown here).

FIGS. 2-9 illustrate, in an exemplary manner, various embodiments of the shape of the edge (16) of the receptacle position (14) for the gauge (26) and preferred orientations of the receptacle position (14). The direction of view is along the spatial Z-direction.

Figure 2:
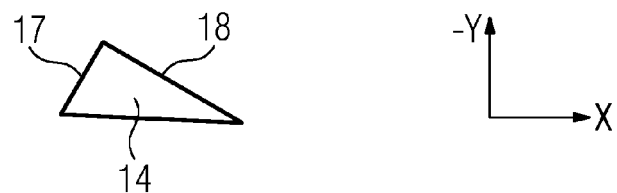
FIGS. 2-9 show receptacle positions for a gauge.

FIG. 2 shows a receptacle position (14), which has the shape of a triangle.

Figure 3:
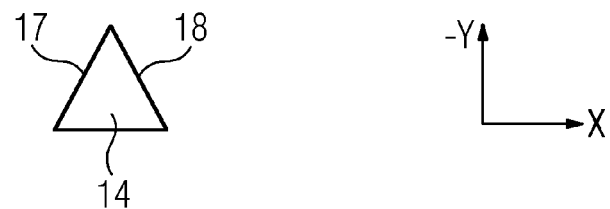

FIG. 3 shows a receptacle position (14), which has the shape of an isosceles triangle.

Figure 4:
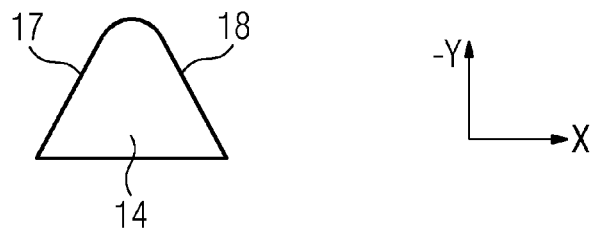

FIG. 4 shows a receptacle position (14), which has the shape of a digon, similar in shape to an isosceles triangle but with a rounded section between the sides.

Figure 5:
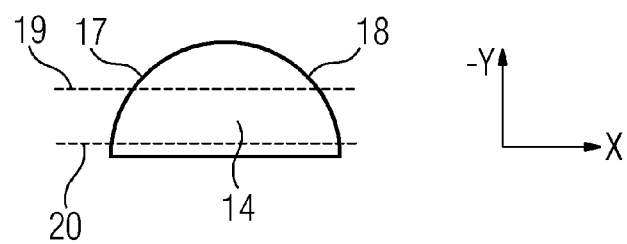

FIG. 5 shows a receptacle position (14) which has the shape of a half circular disk. Additionally, the imaginary lines (19, 20) have been depicted.

Figure 6:
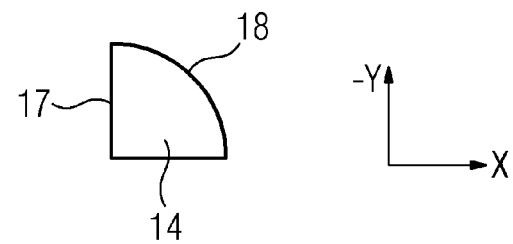

FIG. 6 shows a receptacle position (14), which has the shape of a quarter circular disk.

Figure 7:
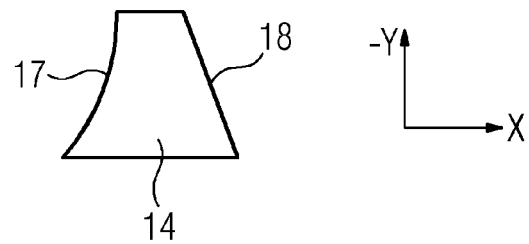

FIG. 7 shows a receptacle position (14), wherein the first edge section (17) extends in a convex arc and the second edge section (18) extends in a straight line.

Figure 8:
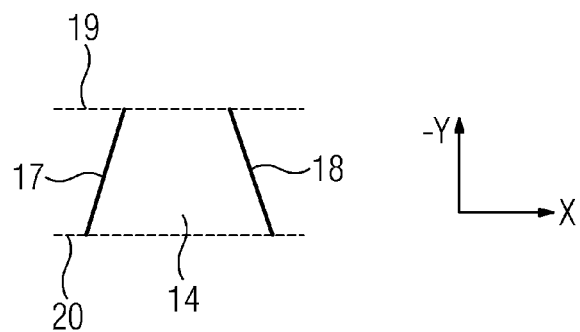
Figure 9:
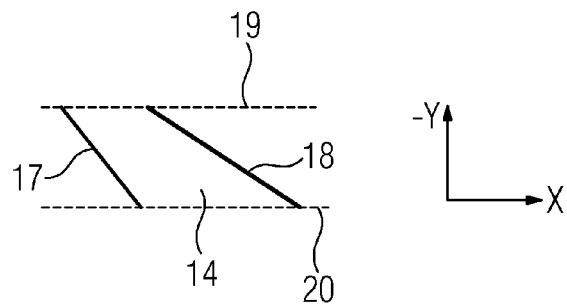

FIG. 8 and FIG. 9 show receptacle positions (14), which are delimited by a first edge section (17) extending in a straight line and a second edge section (18) extending in a straight line, which edge sections are inclined in a characteristic manner in relation to one another, and which are delimited by the imaginary lines (19, 20).

Figure 10:
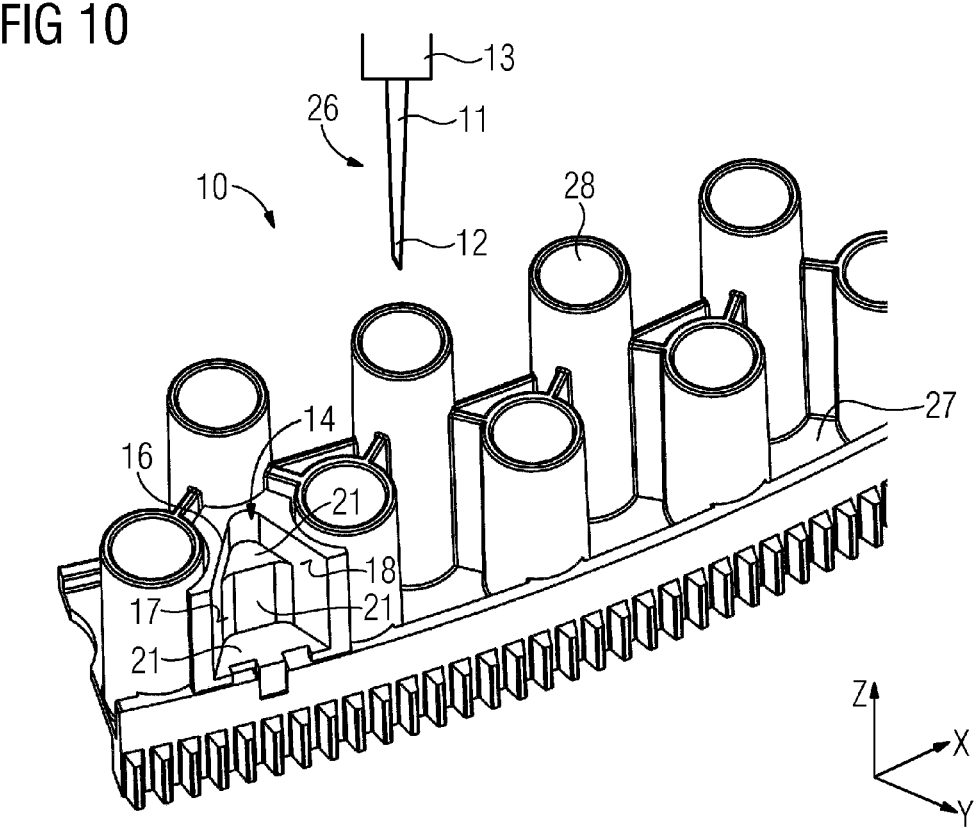
FIGS. 10-12 show apparatus for determining the position, comprising a receptacle position for a gauge for adjusting a pipetting needle relative to a rotatable assembly in an analysis instrument.

FIG. 10 illustrates, in an exemplary manner, a preferred embodiment of the apparatus (10) according to the invention for determining the position for a gauge (26) and a rotatable assembly (27), wherein the gauge (26) is a pipetting needle (11), with a pipetting needle tip (12), fastened to a suspension (13). The apparatus (10) for determining the position is embedded in an analysis instrument (not depicted in any more detail) which is configured to implement a multiplicity of analyses of samples.

The apparatus (10) for determining the position for a gauge (26) comprises a recess which constitutes the receptacle position (14). The receptacle position (14) has an edge (16) with a first (17) and a second edge section (18) and a specifically configured shape with two boundary faces (21) with defined positions in the spatial Z-direction. The boundary faces (21) define a step with the spacing of said faces in the spatial Z-direction, which step encloses a boundary face (21) with a normal in the spatial Y-direction.

The receptacle position (14) is oriented on the rotatable assembly in such a way that the triangle-like shape of the receptacle position (14) opens radially outward. Receptacle positions (28) for receiving sample tubes are situated on the assembly.

Figure 11:
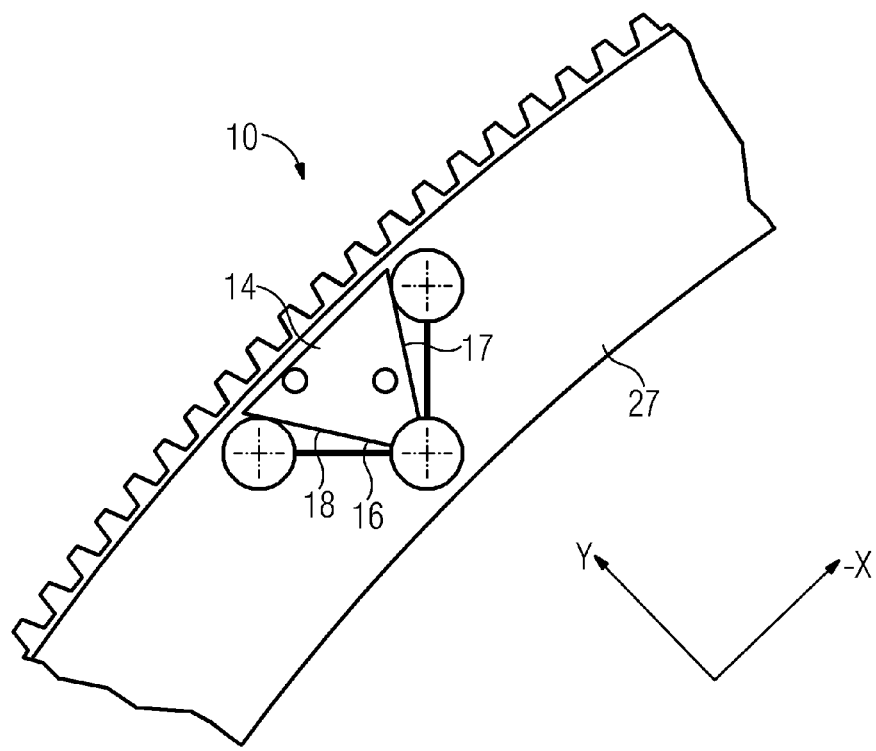

FIG. 11 illustrates, in an exemplary manner, a preferred embodiment of the shape of the edge (16) with a first (17) and a second edge section (18) of the receptacle position (14). The direction of view is along the spatial Z-direction. The receptacle position (14) is oriented on the movable assembly (27), which is embodied as a rotatable assembly, in such a way that the triangle-like shape of the receptacle position (14) opens radially outward.

Figure 12:
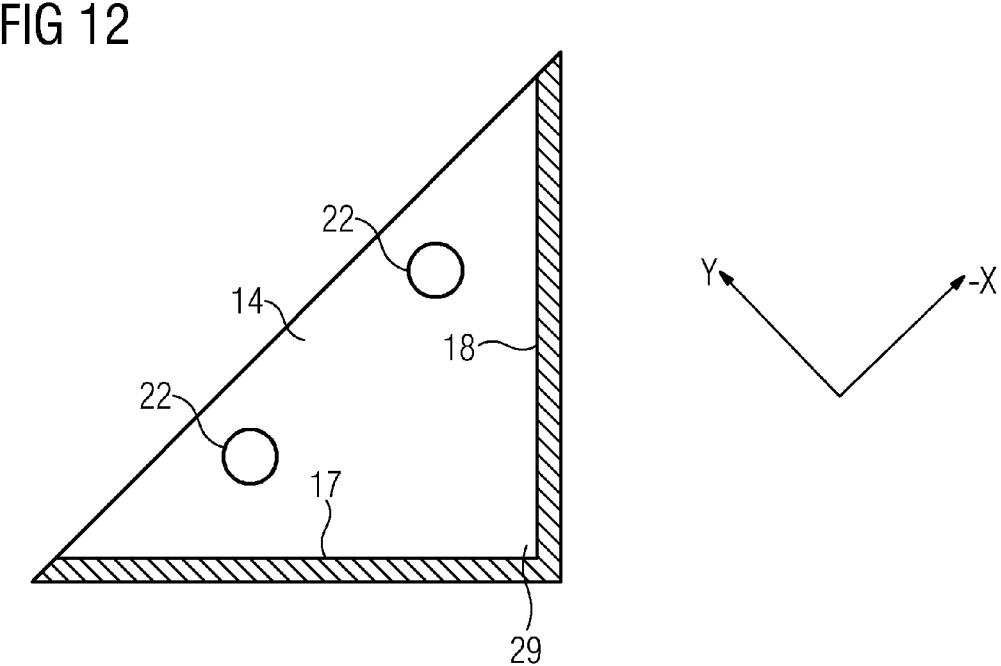

FIG. 12 illustrates, in an exemplary manner, a preferred embodiment of a receptacle position (14) with a first (17) and a second edge portion. The direction of view is along the spatial Z-direction. The receptacle position (14) has connection means (22) for a detachable connection between the receptacle position (14) and a movable assembly (27).

Figure 13:
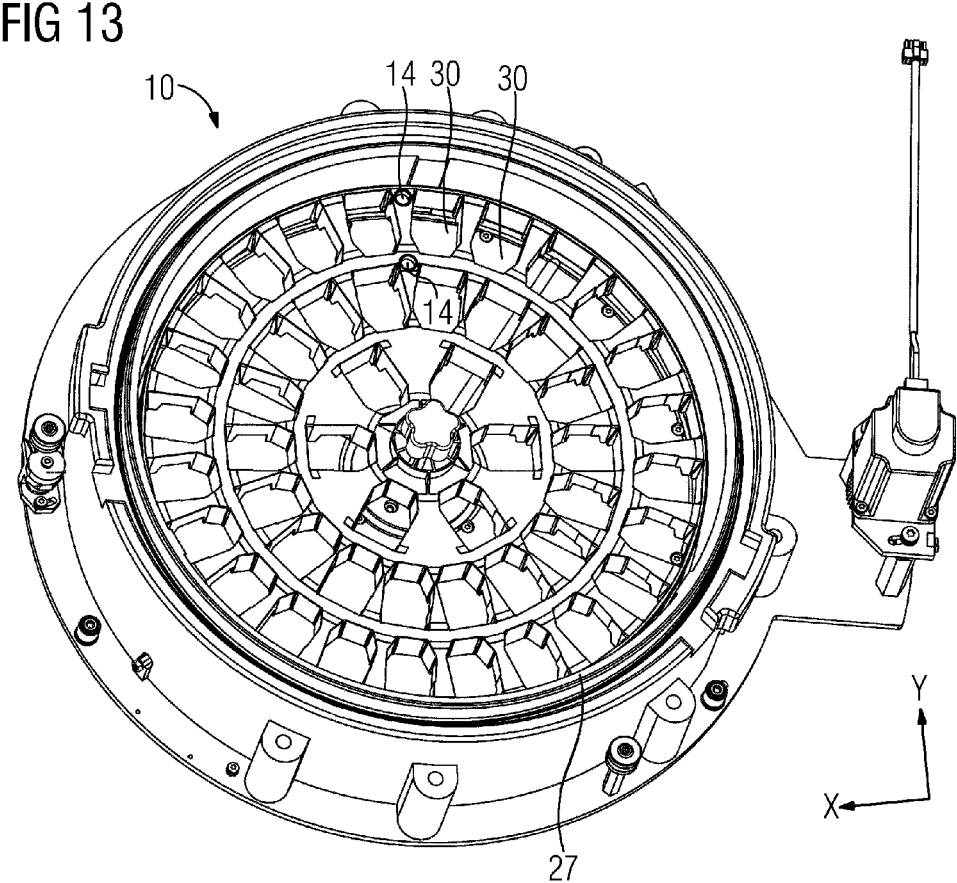
FIGS. 13 and 14 show an alternative embodiment of apparatus for determining the position, comprising a receptacle position.
Figure 14:
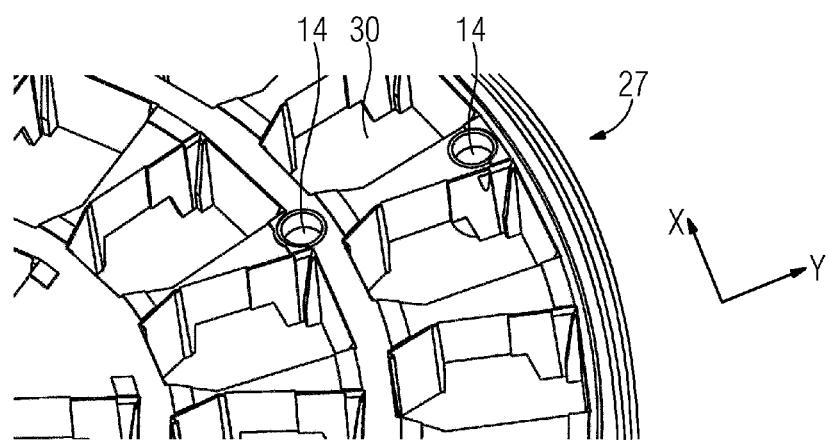

FIGS. 13 and 14 illustrate, in an exemplary manner, a preferred alternative embodiment of the apparatus (10) for determining the position, comprising receptacle positions (14) for a gauge (26), in which the receptacle positions (14) have the shape of a cylinder. In FIG. 13, the direction of view is approximately along the spatial Z-direction; in FIG. 14, it is inclined to the spatial Z-direction. The receptacle positions (14) are attached at different radii on a rotatable assembly (27). The rotatable assembly (27) has receptacle positions (30) for reagent containers, which are arranged concentrically in a plurality of rings on the movable assembly (27).

Figure 15:
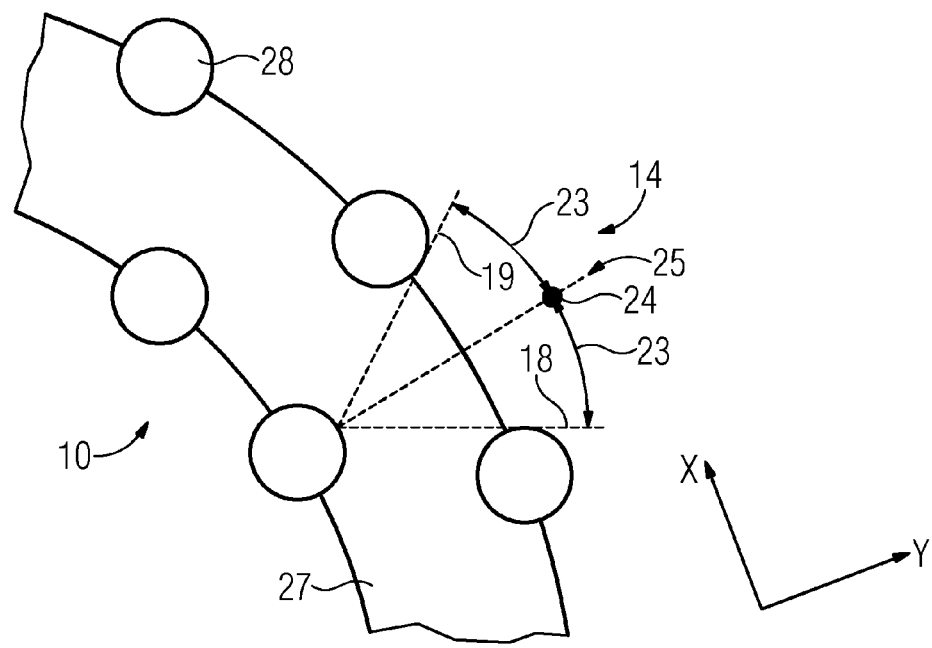
FIG. 15 shows an illustration of an exemplary embodiment of apparatus for determining the position of a gauge.

FIG. 15 illustrates, in an exemplary manner, a preferred embodiment of the apparatus (10) according to the invention for determining the position of a gauge (26). The receptacle position (14) for the gauge (26) is arranged on a rotatable assembly (27). The direction of view is along the spatial Z-direction. The target position (24) of the gauge (26) lies on the bisector (25) of the angle spanned by the edge of the receptacle position (14) and at a defined radial position which is set by means of defined distances (23) between the first (17) and the second edge section (18) of the receptacle position (14). Receptacle positions (28) for sample tubes, which are arranged in two concentric rings, are situated on the movable assembly (27).

FIGS. 16-19 illustrate, in an exemplary manner, various steps of a preferred embodiment of the method according to the invention for determining the position of a gauge (26). The steps can, in part, also be performed in alternative sequences.

Figure 16:
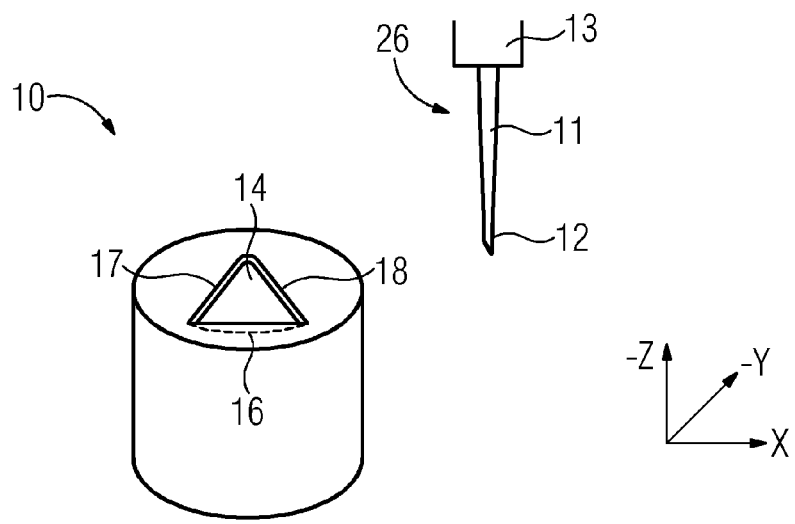
FIGS. 16-19 show illustrations of various steps in a method for determining the position.

Here, FIG. 16 shows apparatus (10) for determining the position, comprising a pipetting needle (11) with a pipetting needle tip (12) and a suspension (13), as well as a receptacle position (14) with a first edge section (17) and a second edge section (18). The receptacle position (14) is integrated into a movable assembly (27). The pipetting needle (11) is situated outside of the receptacle position (14).

Figure 17:
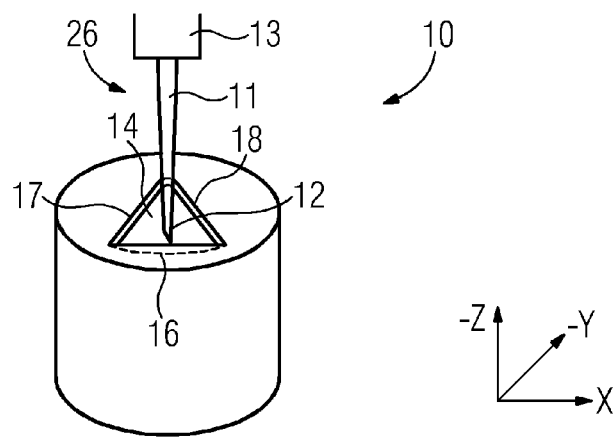

FIG. 17 shows the apparatus (10) depicted in FIG. 16, wherein the pipetting needle (11) is situated in the receptacle position (14). This can be achieved by displacing the pipetting needle (11) in the spatial X- and/or Y- and Z-direction and/or by moving the movable assembly.

Figure 18:
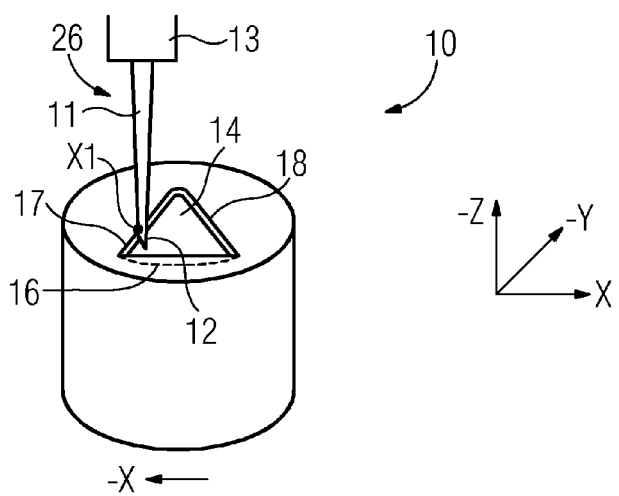

FIG. 18 shows the apparatus (10) depicted in FIG. 16. By means of movement of the movable assembly (27) in the spatial minus X (−X)-direction, a first point X1 is determined by virtue of the pipetting needle (11) approaching, and/or abutting on, the first edge section (17).

Figure 19:
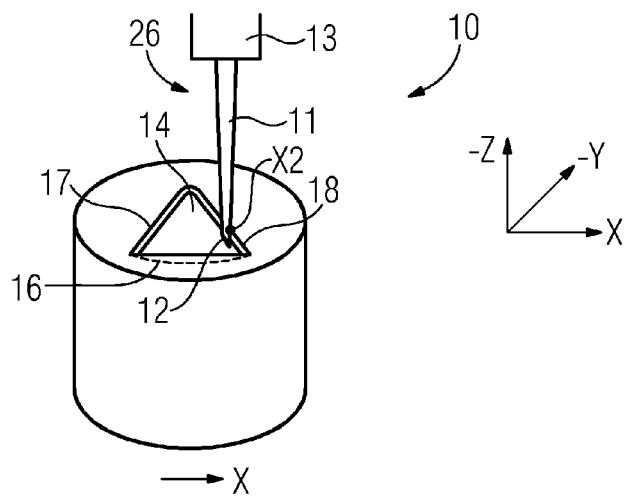

FIG. 19 shows the apparatus (10) depicted in FIG. 16. By means of movement of the movable assembly (27) in the spatial X-direction, a second point X2 is determined by virtue of the pipetting needle (11) approaching, and/or abutting on, the second edge section (18). The position of the pipetting needle (11) can be determined exactly in the spatial X-direction by evaluating X1 and X2. The distance between the points X2 and X1 is established and this enables the determination of the position of the pipetting needle (11) in the spatial Y-direction by assigning the distance between X1 and X2 to a position in the spatial Y-direction as a function of the shape and size of the receptacle position (14).

The described movements of the movable assembly (27) can, for example, be implemented by rotating a rotatably embodied movable assembly (27).

LIST OF REFERENCE SIGNS

10 Apparatus for determining the position
11 Pipetting needle
12 Pipetting needle tip
13 Suspension
14 Receptacle position
16 Edge
17 First edge section
18 Second edge section
19 First imaginary line
20 Second imaginary line
21 Boundary face
22 Connection means
23 Distance
24 Target position
25 Bisector
26 Gauge
27 Movable assembly
28 Receptacle position for sample tubes
29 Point
30 Receptacle position for reagent containers
X Spatial X-direction
Y Spatial Y-direction
Z Spatial Z-direction

What is claimed is:

1. An apparatus for determining the position of an automatically displaceable gauge, said apparatus comprising:
the automatically displaceable gauge;
a first device for displacing the automatically displaceable gauge in a spatial X-direction, which is perpendicular to the longitudinal axis of the automatically displaceable gauge;
a second device for displacing the automatically displaceable gauge in a spatial Z-direction, which extends parallel to the longitudinal axis of the automatically displaceable gauge;
a sensor for identifying an abutment of the automatically displaceable gauge on, or an approach thereof to, an article;
an at least partly bordered receptacle position for the automatically displaceable gauge into which the automatically displaceable gauge is at least partly insertable by displacing the automatically displaceable gauge in the spatial X-direction or Z-direction, wherein the receptacle position is configured as a vertical depression and has two steps within the depression enclosing a boundary face with a normal in a spatial Y-direction; and
a movable assembly, wherein the receptacle position is arranged on the movable assembly.

2. The apparatus as claimed in claim 1, wherein the movable assembly is rotatable.

3. The apparatus as claimed in claim 1, wherein the receptacle position has a first edge section and a second edge section wherein the first and second edge sections delimit the receptacle position in the spatial X-direction in such a way that the receptacle position decreases monotonically between a first imaginary line, which extends parallel to the spatial X-direction, and a second imaginary line, which extends parallel to the spatial X-direction, in the spatial X-direction, which extends tangentially to the movable assembly in the region of the receptacle position.

4. The apparatus as claimed in claim 1, wherein the receptacle position has the shape of a triangle, an isosceles triangle, a digon equal in shape to an isosceles triangle with a rounded section between the sides, a half circular disk, or a quarter circular disk.

5. The apparatus as claimed in claim 1, wherein the receptacle position has a first edge section and a second edge section wherein the first edge section and the second edge section extend in a straight line and converge in a V-shape and wherein the first edge section and the second edge section are symmetrical with respect to a straight extended connection line between a point of rotation of the movable assembly and a point at which the first edge section and the second edge section converge.

6. The apparatus as claimed in claim 1, wherein the receptacle position is configured as a depression in the form of a cylinder or a right circular cylinder.

7. The apparatus as claimed in claim 1, wherein the two steps have a boundary face in the spatial Z-direction.

8. The apparatus as claimed in claim 1, wherein the automatically displaceable gauge is configured as a cylinder or a right circular cylinder or comprises a gripper or a pipetting needle.

9. An analysis instrument comprising a control unit and the apparatus of claim 1.

10. A method for determining the position of an automatically displaceable gauge, comprising:
introducing the automatically displaceable gauge into a receptacle position that is arranged on a movable assembly by displacing the automatically displaceable gauge in a spatial Z-direction, which extends parallel to the longitudinal axis of the automatically displaceable gauge, or in a spatial X-direction, which extends parallel to the movement direction of the movable assembly, or in a spatial Y-direction, which extends perpendicular to the movement direction of the movable assembly, wherein the receptacle position is configured as a vertical depression and has two steps within the depression enclosing a boundary face with a normal in the spatial Y-direction;

moving the movable assembly in a first direction until the automatically displaceable gauge approaches or abuts a first point on a first edge section of the receptacle position;

moving the movable assembly in a second direction until the automatically displaceable gauge approaches or abuts a second point on a second edge section of the receptacle position; and establishing the distance between the first point on the first edge section and the second point on the second edge section of the receptacle position.

11. The method as claimed in claim 10, further comprising:

establishing the position of the automatically displaceable gauge in the spatial X-direction by evaluating the first point on the first edge section or the second point on the second edge section of the receptacle position; and establishing the position of the automatically displaceable gauge in the spatial Y-direction by assigning the established distance between the first and second points to a position in the spatial Y-direction.

12. The method as claimed in claim 10, further comprising:

displacing the automatically displaceable gauge in the spatial Y-direction within the receptacle position;

repeating the moving of the movable assembly in the first direction, the moving of the movable assembly in the second direction, and the establishing of the distance between the first point on the first edge section and the second point on the second edge section; and establishing the position of the automatically displaceable gauge in the spatial Y-direction by assigning the established distances between the first and second points to a position in the spatial Y-direction.

13. The method as claimed in claim 10, wherein the movable assembly is rotatable and wherein the spatial X-direction extends tangentially to the movable assembly and wherein the spatial Y-direction extends radially to the movable assembly.

14. The method as claimed in claim 10, wherein the receptacle position has the shape of a triangle, an isosceles triangle, a digon equal in shape to an isosceles triangle with a rounded section between the sides, a half circular disk, or a quarter circular disk.

15. The method as claimed in claim 10, wherein the first edge section and the second edge section of the receptacle position extend in a straight line and converge in a V-shape and wherein the first edge section and the second edge section are symmetrical with respect to a straight extended connection line between a point of rotation of the movable assembly and a point at which the first edge section and the second edge section converge.

16. The method as claimed in claim 10, wherein the receptacle position is configured as a depression in the form of a cylinder or a right circular cylinder.

17. The method as claimed in claim 10, wherein the two steps have a boundary face in the spatial Z-direction.

18. The method as claimed in claim 10, wherein the automatically displaceable gauge is configured as a cylinder or a right circular cylinder or comprises a gripper or a pipetting needle.

* * * * *